United States Patent
Beyerlein et al.

(10) Patent No.: US 10,342,506 B2
(45) Date of Patent: Jul. 9, 2019

(54) MEDICAL IMAGING DEVICE INCLUDING A POWER TRANSMISSION LINK

(71) Applicant: Siemens Healthcare GmbH, Erlangen (DE)

(72) Inventors: Walter Beyerlein, Bubenreuth (DE); Ottmar Forstel, Pinzberg (DE); Xiao Bo Gao, Shanghai (CN); Joachim Grund-Ruffani, Pinzberg (DE); Winrich Heidinger, Erlangen (DE); Robert Heiter, Fuerth (DE); Elke Jennewein-Wolters, Hoechstadt an der Aisch (DE); Thomas Luthardt, Bamberg (DE); Stefan Waffler, Buckenhof (DE)

(73) Assignee: Siemens Healthcare GmbH, Erlangen (DE)

( * ) Notice: Subject to any disclaimer, the term of this patent is extended or adjusted under 35 U.S.C. 154(b) by 255 days.

(21) Appl. No.: 15/113,107

(22) PCT Filed: Jan. 15, 2015

(86) PCT No.: PCT/EP2015/050674
§ 371 (c)(1),
(2) Date: Jul. 21, 2016

(87) PCT Pub. No.: WO2015/113830
PCT Pub. Date: Aug. 6, 2015

(65) Prior Publication Data
US 2017/0007197 A1    Jan. 12, 2017

(30) Foreign Application Priority Data
Jan. 31, 2014  (DE) .......... 10 2014 201 805

(51) Int. Cl.
*A61B 6/03*     (2006.01)
*A61B 6/00*     (2006.01)

(52) U.S. Cl.
CPC ............. *A61B 6/56* (2013.01); *A61B 6/032* (2013.01); *A61B 6/035* (2013.01); *A61B 6/54* (2013.01); *A61B 6/542* (2013.01)

(58) Field of Classification Search
CPC ........... A61B 6/032; A61B 6/035; A61B 6/54; A61B 6/542; A61B 6/56; A61B 6/563; A61B 6/566
(Continued)

(56) References Cited

U.S. PATENT DOCUMENTS 5,226,064 A * 7/1993 Yahata ............... H05G 1/10
378/101
5,608,771 A * 3/1997 Steigerwald ........ A61B 6/56
378/15

(Continued)

FOREIGN PATENT DOCUMENTS

CN   102163915 A   8/2011
CN   102570570 A   7/2012
(Continued)

OTHER PUBLICATIONS

German Office Action dated Nov. 19, 2014.
(Continued)

*Primary Examiner* — Allen C. Ho
(74) *Attorney, Agent, or Firm* — Harness, Dickey & Pierce, P.L.C.

(57) ABSTRACT

A medical imaging device includes a stationary device part and a moveable device part moveably mounted for this purpose. A power source is arranged on the stationary device part. A number of main electrical consumers, a number of secondary electrical consumers, and an energy storage
(Continued)

device are arranged on the moveable device part. A power transmission link, arranged between the stationary device part and the moveable device part, is designed to transmit power from the stationary device part to the moveable device part. On the stationary device part, an energy emitting component of the power transmission link is connected to the power source and on the moveable device part, an energy receiving component of the power transmission link is switchably connected to the main consumer and to the secondary consumer via switching device(s), and to the energy storage device. The energy storage device is switchably connected to the secondary consumer.

16 Claims, 2 Drawing Sheets

(58) Field of Classification Search
USPC .......................................... 378/15, 91, 101
See application file for complete search history.

(56) References Cited

U.S. PATENT DOCUMENTS

| | | | | |
|---|---|---|---|---|
| 5,808,376 | A * | 9/1998 | Gordon | G01T 1/175 307/64 |
| 6,590,953 | B2 * | 7/2003 | Suzuki | A61B 6/035 310/211 |
| 6,975,698 | B2 * | 12/2005 | Katcha | A61B 6/56 378/101 |
| 7,054,411 | B2 * | 5/2006 | Katcha | A61B 6/56 336/105 |
| 7,197,113 | B1 * | 3/2007 | Katcha | A61B 6/032 378/101 |
| 7,425,096 | B2 * | 9/2008 | Beyerlein | A61B 6/56 378/101 |
| 7,432,622 | B2 * | 10/2008 | Griepentrog | H01F 38/18 307/104 |
| 7,447,293 | B2 * | 11/2008 | Kasuya | A61B 6/035 378/103 |
| 7,522,705 | B2 * | 4/2009 | Katcha | A61B 6/032 378/102 |
| 7,593,502 | B2 * | 9/2009 | Katcha | A61B 6/032 378/101 |
| 7,634,046 | B2 * | 12/2009 | Krumme | A61B 6/56 378/101 |
| 7,717,619 | B2 * | 5/2010 | Katcha | G08C 17/04 378/15 |
| 7,826,586 | B2 * | 11/2010 | Nakayama | A61B 6/035 378/101 |
| 7,848,482 | B2 * | 12/2010 | Nakayama | A61B 6/035 378/101 |
| 7,868,723 | B2 * | 1/2011 | Dobbs | A61B 6/56 336/84 C |
| 7,880,569 | B2 * | 2/2011 | Krumme | A61B 6/56 333/245 |
| 7,899,149 | B2 * | 3/2011 | Krumme | H04L 25/08 378/15 |
| 7,899,150 | B2 * | 3/2011 | Beyerlein | A61B 6/56 378/101 |
| 7,957,786 | B2 * | 6/2011 | Katcha | A61B 6/56 336/145 |
| 8,129,865 | B2 * | 3/2012 | Krumme | A61B 6/56 307/104 |
| 8,164,929 | B2 * | 4/2012 | Zimpfer | A61B 6/56 363/34 |
| 8,194,818 | B2 * | 6/2012 | Meng | A61B 6/56 378/19 |
| 8,218,726 | B2 * | 7/2012 | Bressel | A61B 6/032 378/103 |
| 8,242,639 | B2 * | 8/2012 | Krumme | A61B 6/56 307/104 |
| 8,295,431 | B2 * | 10/2012 | Lindorfer | H04L 25/4906 378/15 |
| 8,340,242 | B2 * | 12/2012 | Grottel | A61B 6/032 378/15 |
| 8,350,655 | B2 * | 1/2013 | Dobbs | A61B 6/56 336/115 |
| 8,379,797 | B2 * | 2/2013 | Abenaim | A61B 6/027 378/103 |
| 8,447,010 | B2 * | 5/2013 | Reichel | A61B 6/032 378/15 |
| 8,494,112 | B2 * | 7/2013 | Reichel | A61B 6/56 378/15 |
| 8,519,721 | B2 * | 8/2013 | Krumme | H02J 50/12 324/652 |
| 8,581,437 | B2 * | 11/2013 | Delforge | A61B 6/56 307/11 |
| 8,581,553 | B2 * | 11/2013 | Takaichi | H02J 9/061 320/132 |
| 8,594,480 | B2 * | 11/2013 | Krumme | A61B 6/56 333/113 |
| 8,824,624 | B2 * | 9/2014 | Loef | A61B 6/56 378/15 |
| 8,861,678 | B2 * | 10/2014 | Liu | H05G 1/08 378/91 |
| 8,861,681 | B2 * | 10/2014 | Caiafa | H02M 3/337 378/101 |
| 8,891,733 | B2 * | 11/2014 | Liu | A61B 6/42 378/91 |
| 8,987,944 | B2 * | 3/2015 | Friesner | A61B 6/032 307/104 |
| 9,008,275 | B2 * | 4/2015 | Hanlon | H05G 1/58 378/101 |
| 9,080,606 | B2 * | 7/2015 | Kalenyak | A61B 6/035 |
| 9,084,335 | B2 * | 7/2015 | Mekonnen | H05G 1/10 |
| 9,112,366 | B2 * | 8/2015 | Krumme | H02J 5/005 |
| 9,119,592 | B2 * | 9/2015 | Katcha | A61B 6/03 |
| 9,138,195 | B2 * | 9/2015 | Krupica | G01N 23/046 |
| 9,144,412 | B2 * | 9/2015 | Poulo | A61B 6/56 |
| 9,149,240 | B2 * | 10/2015 | Nakai | A61B 6/032 |
| 9,154,014 | B2 * | 10/2015 | Kalenyak | A61B 6/035 |
| 9,161,731 | B2 * | 10/2015 | Foerner | A61B 6/44 |
| 9,170,378 | B2 * | 10/2015 | Bowman | G02B 6/3604 |
| 9,186,120 | B2 * | 11/2015 | Zimpfer | A61B 6/56 |
| 9,368,272 | B2 * | 6/2016 | Dobbs | A61B 6/032 |
| 9,375,193 | B2 * | 6/2016 | Luthardt | H05G 1/08 |
| 9,438,120 | B2 * | 9/2016 | Caiafa | H02M 3/33507 |
| 9,636,078 | B2 * | 5/2017 | Ergler | A61B 6/56 |
| 9,713,238 | B2 * | 7/2017 | Krupica | H05G 1/10 |
| 9,715,962 | B2 * | 7/2017 | Beyerlein | A61B 6/56 |
| 9,722,429 | B2 * | 8/2017 | Weedon | A61B 6/56 |
| 9,737,273 | B2 * | 8/2017 | Gregerson | A61B 6/035 |
| 9,757,089 | B2 * | 9/2017 | Reichel | A61B 6/032 |
| 9,853,694 | B2 * | 12/2017 | Sloutsky | H04B 5/0075 |
| 9,888,886 | B2 * | 2/2018 | Distler | A61B 6/035 |
| 10,028,320 | B2 * | 7/2018 | Poulo | H04W 76/14 |
| 10,048,337 | B2 * | 8/2018 | Yokoi | A61B 6/032 |
| 2010/0220837 | A1 | 9/2010 | Bressel | |
| 2011/0206272 | A1 | 8/2011 | Takaichi | |

FOREIGN PATENT DOCUMENTS

| | | |
|---|---|---|
| CN | 102802527 A | 11/2012 |
| CN | 102835971 A | 12/2012 |
| CN | 102860835 A | 1/2013 |
| CN | 202801644 U | 3/2013 |
| DE | 102010042565 A1 | 4/2012 |

OTHER PUBLICATIONS

International Search Report and Written Opinion dated Apr. 2, 2015.
Chinese Office Action dated May 31, 2018 issued in Chinese Application No. 201580006658.6.

(56) References Cited

OTHER PUBLICATIONS

Chinese Office Action dated Mar. 22, 2019 issued in corresponding Chinese Application No. 201580006658.6 (English translation provided).

* cited by examiner

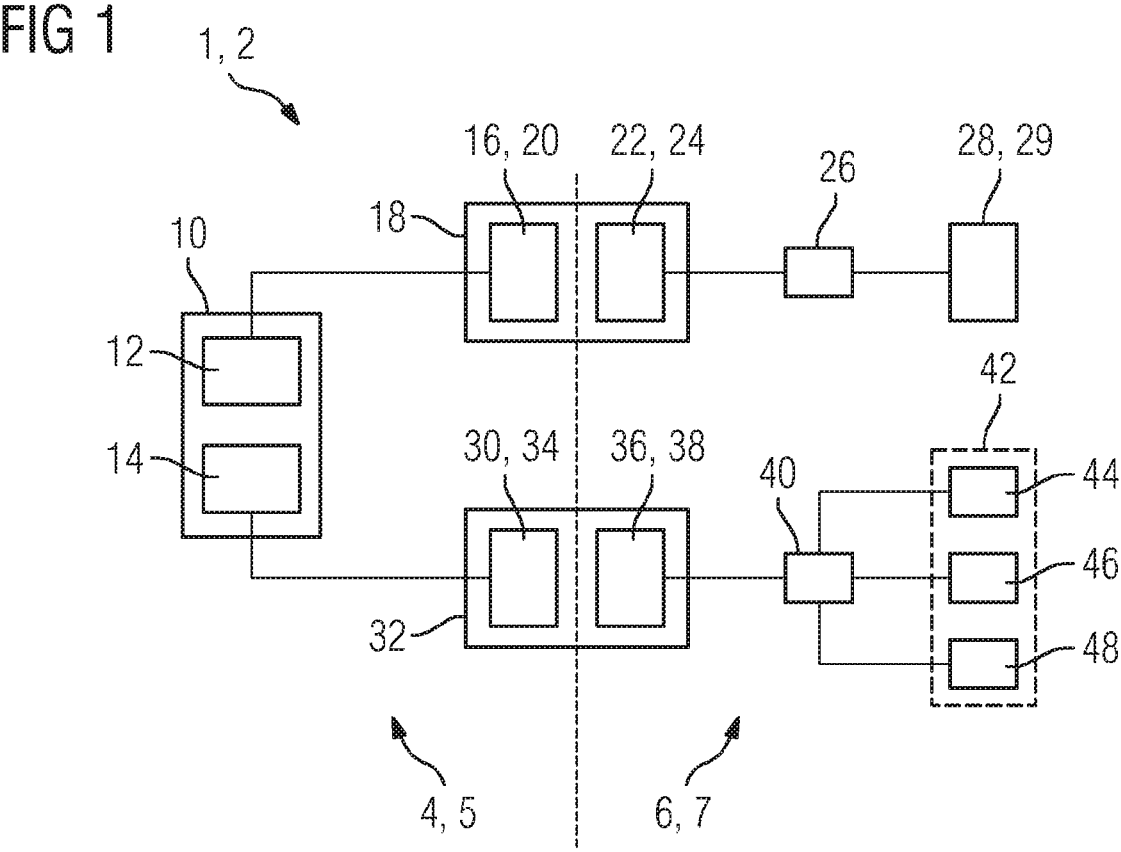

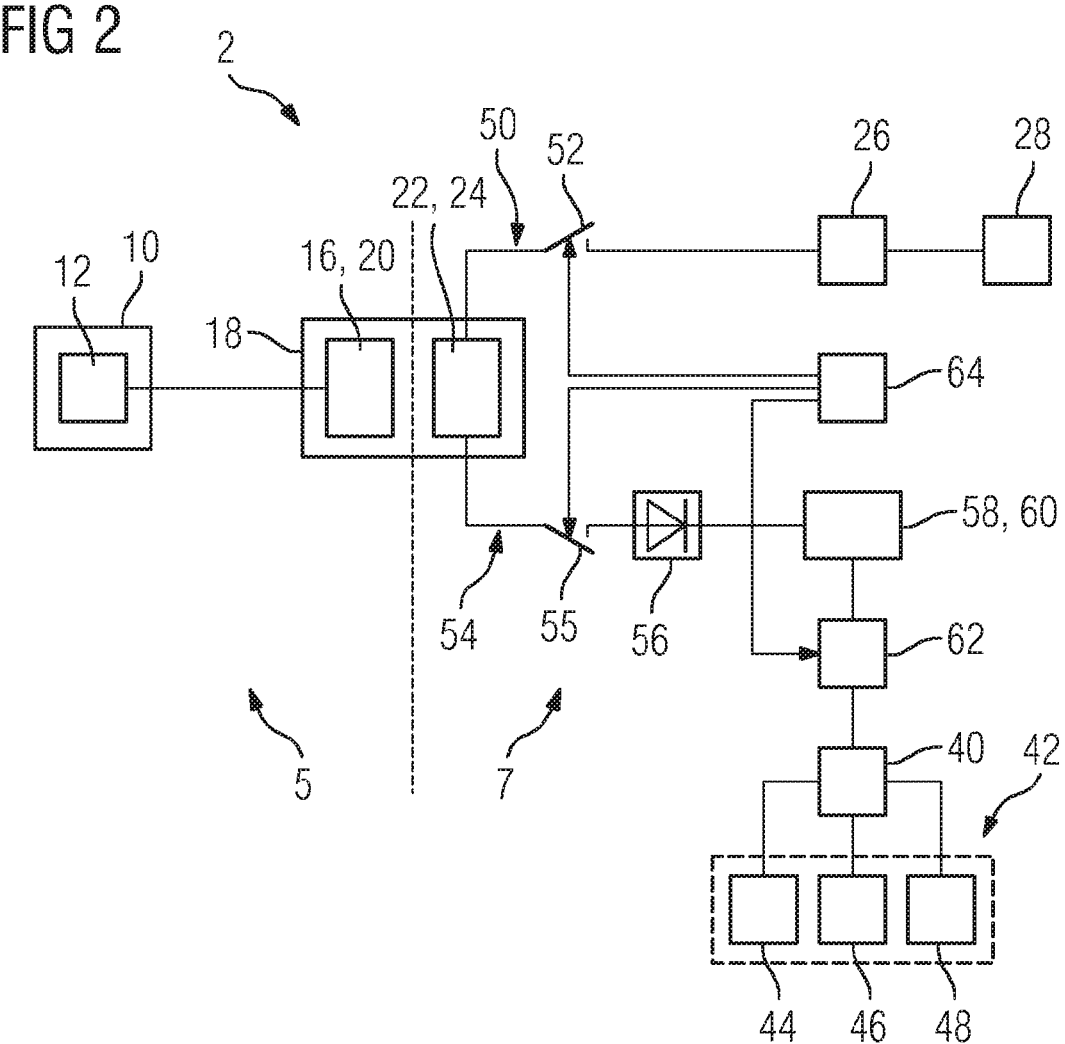

MEDICAL IMAGING DEVICE INCLUDING A POWER TRANSMISSION LINK

PRIORITY STATEMENT

This application is the national phase under 35 U.S.C. § 371 of PCT International Application No. PCT/EP2015/050674 which has an International filing date of Jan. 15, 2015, which designated the United States of America and which claims priority to German patent application number DE 102014201805.6 filed Jan. 31, 2014, the entire contents of which are hereby incorporated herein by reference.

FIELD

An embodiment of invention generally relates to a medical imaging device comprising a fixed device section and a movable device section movably mounted for this purpose. In at least one embodiment, a power source for providing power is disposed on the fixed device section, wherein a number of main electrical consuming devices and a number of secondary electrical consuming devices are disposed on the movable device section. Further, in at least one embodiment, a power transmission link designed to transmit power from the fixed device section to the movable device section is disposed between the fixed device section and the movable device section. At least one embodiment of invention also generally relates to a method for supplying power to such a medical imaging device.

BACKGROUND

For operating a medical imaging device, e.g. a computed tomography scanner, in many cases power has to be transmitted from a fixed device section to a movable device section. Often one or more radiation sources such as an X-ray emitter, for example, and a plurality of detectors are disposed on the movable device section, e.g. the rotating ring of a computed tomography scanner. The detectors may also be connected to imaging electronics likewise disposed on the movable device section. During operation, the movable device section can execute a movement allowing it to image one or more body parts of a patient from different perspectives.

During operation, the radiation source(s), the detectors and possibly various other consuming devices such as e.g. imaging electronics, control electronics, a cooling system, or a rotating anode drive, must be supplied with power, the power having to be transmitted from the fixed to the movable device section. Particularly in the case of a computed tomography scanner having a rotating ring which performs a plurality of rotations often in rapid succession, supplying them via a cable is not practicable, which means that a slip ring contact or inductive transfer is commonly used for this purpose.

In a computed tomography scanner, because of the differing power requirement, two separate power transmission links are normally used for supplying the X-ray emitter and for supplying the detectors and associated electronics.

In order to operate at optimum resolution, many detector types, particularly those based on doped semiconductors, require a setup time, with voltage applied, until an equilibrium has been established in the active material in the detector, and the most favorable operating point has been reached. The detectors are therefore usually kept energized even between the individual scanning operations, resulting in a relatively constant consumption baseload of up to a few kW.

The X-ray emitter, on the other hand, only requires energy during a scanning operation, but this can range from 20 kW to over 200 kW depending on the type of scan. Intensified cooling may also be necessary during a scanning operation. As this power requirement differs significantly from the baseload constituted by the detectors, the X-ray emitter is preferably supplied by a separate power transmission link.

SUMMARY

The inventors have recognized that, due to the increasing space requirement in the rotating ring for detectors of ever higher resolution together with constructional constraints, it is becoming necessary to dispose the components in the rotating ring in as space-saving a manner as possible.

At least one embodiment of the invention specifies a medical imaging device having a fixed and a movable device section and enabling power to be transmitted from the fixed device section to the movable device section in as simple and compact a manner as possible. At least one embodiment of the invention also specifies a method for supplying power to a medical imaging device of this kind.

At least one embodiment includes a medical imaging device, comprising a fixed device section and a movable device section movably mounted for this purpose, wherein a power source for providing electrical energy is disposed on the fixed device section, wherein a number of main electrical consuming devices, a number of secondary electrical consuming devices, and an energy storage device are disposed on the movable device section, wherein a power transmission link designed to transmit power from the fixed device section to the movable device section is disposed between the fixed device section and the movable device section, wherein an energy supplying component of the power transmission link is connected to the power source on the fixed device section, wherein an energy receiving component of the power transmission link is switchably connected via a switching device to the/each main consuming device and to the/each secondary consuming device on the movable device section and is connected to the energy storage device, and wherein the energy storage device is switchably connected to the/each secondary consuming device.

At least one embodiment includes a method for supplying energy to a medical imaging device of the type described above, wherein the energy storage device is charged by the power source via the power transmission link, wherein, during baseload operation, the/each secondary electrical consuming device is supplied by the power source via the power transmission link, and wherein, during main load operation, the/each main electrical consuming device is supplied by the power source via the power transmission link while the/each secondary electrical consuming device is supplied by the energy storage device. In particular, the method is to be carried out by the switching device disposed in the power connections on the movable device section. For correct operation of the equipment, particular attention must be paid to the switching times of the switching device for the transition from baseload operation to main load operation and vice versa.

BRIEF DESCRIPTION OF THE DRAWINGS

An example embodiment of the invention will now be explained in greater detail with reference to the accompanying drawings in which:

FIG. 1 shows a simplified schematic diagram for the supply of power to the consuming devices disposed on the rotating ring of a computed tomography scanner according to the prior art, and FIG. 2 shows a simplified schematic diagram for the supply of power to the consuming devices disposed on the rotating ring of a computed tomography scanner according to an embodiment of the invention.

Corresponding parts and variables are provided with the same reference characters in each case.

DETAILED DESCRIPTION OF THE EXAMPLE EMBODIMENTS

At least one embodiment includes a medical imaging device, comprising a fixed device section and a movable device section movably mounted for this purpose, wherein a power source for providing electrical energy is disposed on the fixed device section, wherein a number of main electrical consuming devices, a number of secondary electrical consuming devices, and an energy storage device are disposed on the movable device section, wherein a power transmission link designed to transmit power from the fixed device section to the movable device section is disposed between the fixed device section and the movable device section, wherein an energy supplying component of the power transmission link is connected to the power source on the fixed device section, wherein an energy receiving component of the power transmission link is switchably connected via switching device to the/each main consuming device and to the/each secondary consuming device on the movable device section and is connected to the energy storage device, and wherein the energy storage device is switchably connected to the/each secondary consuming device.

At least one embodiment includes a method for supplying energy to a medical imaging device of the type described above, wherein the energy storage device is charged by the power source via the power transmission link, wherein, during baseload operation, the/each secondary electrical consuming device is supplied by the power source via the power transmission link, and wherein, during main load operation, the/each main electrical consuming device is supplied by the power source via the power transmission link while the/each secondary electrical consuming device is supplied by the energy storage device. In particular, the method is to be carried out by the switching device disposed in the power connections on the movable device section. For correct operation of the equipment, particular attention must be paid to the switching times of the switching device for the transition from baseload operation to main load operation and vice versa.

The advantages cited for the medical imaging device and its further developments can be applied analogously to the method and its further developments.

In particular, the power source can be designed to produce different powers. Here and in the following description, connection is to be understood as meaning in particular an electrically conductive connection. Accordingly, a switchable connection device that a connection is established via a particular switching state of the one or more switching devices, and another switching state breaks such a connection.

An energy supplying component is to be understood as meaning a component of the power transmission link which, during operation of the medical imaging device, supplies power to another component of the power transmission link which consumes the power during operation. In particular, the connection from the energy receiving component of the power transmission link to the energy storage device can also be switchable via at least one switching device.

A concept of at least one embodiment of the invention is that the power requirement of a main electrical consuming device often differs from the power requirement of a secondary electrical consuming device, and is often considerably higher, but also of much shorter duration, and accordingly the two different types of consuming device are often supplied by different power transmission links. However, particularly in such a case—a high, transient power requirement of the/each main consuming device—the power transmission link remains unused for the/each main consuming device for most of the time during operation of the medical imaging device. This under-utilization is a particularly important factor in the case of a device in which, for advantageous operation, a number of secondary consuming devices must preferably be continuously supplied with power, and the equipment must accordingly not be switched off between individual scanning operations.

In contrast, it is proposed by at least one embodiment of the invention to provide a connection from an energy receiving component of the power transmission link on the movable device section both to the/each main consuming device and to the/each secondary consuming device. This allows the/each secondary consuming device to be supplied via the power transmission link while the/each main consuming device is not in operation. If the/each main consuming device is in operation, it can be supplied via the power transmission link. The/each secondary consuming device can now be connected to the energy storage device and supplied via it. The switchable connection from the energy storage device to the energy receiving component of the power transmission link allows the energy storage device to be charged in times of low capacity utilization of the power transmission link.

This obviates the need for a separate power transmission link. It also enables any other components connected downstream of the energy consuming component on the movable device section, such as a rectifier, for example, to be shared. By the sharing of such components by the/each main consuming device and the/each secondary consuming device, a component assigned to the eliminated power transmission link can likewise be dispensed with. These savings increase the available space on the movable section.

The power source preferably comprises a converter and/or a transformer. This allows the power source to provide different powers.

A main electrical consuming device is preferably designed as a radiation source. The proposed power transmission is particularly advantageous for meeting the power requirement of the radiation source of a medical imaging device.

A secondary electrical consuming device is preferably designed as a radiation detector or a motor or a data processing unit. In particular, the motor can drive a rotating anode or a fan. The proposed power transmission is particularly advantageous for providing the baseload which, in a medical imaging device, can arise from a radiation detector or a motor or a data processing unit. This applies particularly to a secondary consuming device constituted by a radiation detector which must be continuously supplied with power during operation of the equipment.

It has been found advantageous for a transformer and/or a rectifier to be disposed in the switching path between the/each main consuming device and the power transmission link and between the/each secondary consuming device and the power transmission link. Disposing them in the switching path is to be understood as meaning that a connection switchable via switching device exists between the power transmission link and the respective main or secondary consuming device, the connection passing via a transformer and/or a rectifier in at least one switching state. A rectifier is particularly advantageous if the power transmission link is AC voltage operated, but a number of main and/or secondary consuming devices require a DC voltage. A rectifier can preferably be used here for a plurality of main and/or secondary consuming devices. A transformer is particularly advantageous if the AC voltage provided by the power transmission link is to be matched to an operating voltage of a main or secondary consuming device. A transformer can preferably be used here for a plurality of main and/or secondary consuming devices.

In an advantageous embodiment of the invention, the energy storage device is designed to maintain baseload operation of the/each secondary consuming device for at least a predefined time in the event of failure of the power source. The predefined time can be selected so as to allow safe and orderly shutdown of the equipment. In particular, the time can be selected such that image data of a medical scan can still be fully stored, and a fan can bring components that may be heated by radiation of the radiation source, or the radiation source itself, to a safe temperature range.

The energy storage device advantageously comprises a battery and/or a capacitor. A battery or capacitor is a reliable energy storage device and can be charged or discharged relatively quickly, which meets the requirements in a medical device particularly well. In particular, a transformer and/or a rectifier can be disposed in the switching path between the energy storage device and the power transmission link.

In another advantageous embodiment of the invention, the power transmission link comprises a slip ring contact and/or a number of transmission coils. In particular, the energy supplying component and the energy receiving component can each have a number of the transmission coils. Using a slip ring contact, the required power can be transmitted reliably and with low heat dissipation from the fixed to the movable device section, even while the latter is moving. The transmission coils enable power to be inductively transmitted from the fixed to the movable device section, which is particularly advantageous in the case of rapid movement of the movable device section relative to the fixed device section.

The movable device section is preferably mounted so as to rotate about an axis. The rotation about an axis and the possible scan perspectives resulting therefrom permit a large number of imaging methods that are frequently used in a medical context. In particular, a component of the fixed device section can be displaced axially relative to the movable device section, thereby also providing an extensive axial degree of freedom for a scan.

The medical imaging device is preferably designed as a computed tomography scanner, wherein the fixed device section comprises a support frame and the movable device section comprises a rotating ring, wherein the/each main electrical consuming device is designed as an X-ray tube, and wherein a secondary consuming device is designed as an X-ray detector. The supply of power proposed in the invention is particularly advantageous for the requirements in a computed tomography scanner, due particularly to the associated space saving on the rotating ring, which space saving can be utilized for increasing the number of detector modules.

The energy storage device is preferably supplied during baseload operation, while the/each secondary electrical consuming device is simultaneously supplied at least intermittently. In particular this can mean that, during baseload operation, more power is transmitted at least intermittently via the power transmission link than the/each secondary consuming device can consume, so that the excess can be used for charging the energy storage device. During baseload operation, the power required by the/each secondary consuming device is much lower than the power required by the/each main consuming device during main load operation and for which the power transmission link must preferably be at least designed. Accordingly, an existing transmission capacity can be used for charging the energy storage device.

In another advantageous embodiment of the invention, the medical imaging device comprises a control unit connected to the switching device and which is designed to carry out the method described above. The connection of the control unit to the switching device relates to the possibility of transmitting a control signal, which can take place electrically, electromagnetically or optically.

FIG. 1 shows a simplified schematic diagram of a power supply arrangement in a medical imaging device 1 in the form of a computed tomography scanner 2 according to the prior art. The fixed device section 4 is here constituted by the support frame 5, the movable device section 6 movably mounted for this purpose by the rotating ring 7. Disposed on the support frame 5 is a power source 10 comprising a high-voltage converter 12 and an intermediate-voltage converter 14. The high-voltage converter 12 is connected to the energy supplying component 16 of the power transmission link 18. The energy supplying component 16 comprises a transmission coil 20 which can inductively transmit energy to the energy receiving component of the power transmission link 18, which component is disposed on the rotating ring 7. The energy receiving component 22 comprises a transmission coil 24, and is connected to a high-voltage transformer 26 which is connected to the X-ray tube 28. The X-ray tube 28 constitutes the main consuming device 29 of the computed tomography scanner 2.

The intermediate-voltage converter 14 is connected to the energy supplying component 30 of the power transmission link 32. The energy supplying component 30 comprises a transmission coil 34 which can inductively transmit energy to the energy receiving component 36 of the power transmission link 32, which component is disposed on the rotating ring 7. The energy receiving component 36 comprises a transmission coil 38 and is connected to a distributor module 40 from which the secondary consuming devices 42 of the computed tomography scanner 2 can be supplied with power. The secondary consuming devices 42 comprise an X-ray detector 44, an electronic data processing unit 46 and a fan 48.

During operation of the computed tomography scanner 2, the secondary consuming devices 42 are continuously supplied via the power transmission link 32, wherein the X-ray tube 28 is only supplied with high power for a short operating period of between a few seconds and barely a minute via the power transmission link 18 in each case.

FIG. 2 shows a simplified schematic diagram of a power supply arrangement in a computed tomography scanner 2 according to an embodiment of the invention. The power source on the support frame 5 has a high-voltage converter 12 which is connected to the energy supplying component 16 of the power transmission link 18. The energy supplying component 16 comprises a transmission coil 20 which can inductively transmit energy to the energy receiving component 22 of the power transmission link 18, which component is disposed on the rotating ring 7. The energy receiving component 22 comprises a transmission coil 24. A switching path 50 in which a switch 52 is disposed extends from the energy receiving component 22 of the power transmission link 18 via the high-voltage transformer 26 to the X-ray tube 28, and another switching path 54 passes via a switch 55 to a rectifier 56. Connected to the rectifier 56 is an energy storage device 60 in the form of a capacitor 58 and, in parallel therewith, a step-down converter 62. Connected to the output of the step-down converter 62 is the distributor module 40 from which the secondary consuming devices 42 can be supplied with power. The secondary consuming devices 42 comprise an X-ray detector 44, an electronic data processing unit 46 and a fan 48.

During baseload operation of the converter, the switch is open and the switch 55 is closed. Only the secondary consuming devices 42 draw power from the power transmission link 18 via the switching path 54, wherein the capacitor 58 is also charged. During main load operation, the switch 52 is closed, and the switch 55 is open, the power of the energy receiving component 22 of the power transmission link 18 is therefore supplied to the X-ray tube 28 via the high-voltage transformer 26. The secondary consuming devices 42 are now supplied with power by the capacitor 58, the step-down converter 62 controlling the supply of power via its switch, wherein it receives a control signal from a control unit 64. The control unit 64 also controls, via its switches 52 and 55, the transition between baseload and main load operation. A power transmission link 32 can therefore be eliminated as compared to the prior art.

Although the invention has been illustrated and described in detail by the preferred embodiment, the invention is not limited by this example. Other variations may be inferred therefrom by those skilled in the art without departing from the scope of protection sought for the invention.

What is claimed is:

1. A medical imaging device, comprising:
    a fixed device section;
    a movable device section, movably mounted;
    a power source to provide power, disposed on the fixed device section;
    a number of main electrical consuming devices, a number of secondary electrical consuming devices, and an energy storage device, each disposed on the movable device section;
    at least one switching device; and
    a power transmission link including an energy supplying component and an energy receiving component, configured to transmit power from the fixed device section to the movable device section, disposed between the fixed device section and the movable device section, the energy supplying component on the fixed device section, being connected to the power source, and the energy receiving component on the movable device section being switchably connected to each of the number of main electrical consuming devices and to each of the number of secondary electrical consuming devices via the at least one switching device and being switchably connected to the energy storage device, and the energy storage device being switchably connected to each of the number of secondary electrical consuming devices.

2. The medical imaging device of claim 1, wherein the power source comprises at least one of a converter and a transformer.

3. The medical imaging device of claim 2, wherein a main electrical consuming device comprises a radiation source.

4. The medical imaging device of claim 2, further comprising:
    a computed tomography scanner, wherein the fixed device section comprises a support frame and the movable device section comprises a rotating ring, wherein each of the number of main electrical consuming devices comprises an X-ray tube, and wherein a secondary electrical consuming device comprises an X-ray detector.

5. The medical imaging device of claim 2, further comprising a control unit, connected to the at least one switching device, configured to at least:
    switchably connect the energy storage device to each of the number of secondary electrical consuming devices;
    charge the energy storage device by the power source via the power transmission link;
    supply, during baseload operation, each of the number of secondary electrical consuming devices from the power source via the power transmission link; and
    supply, during main load operation, each of the number of main electrical consuming devices by the power source via the power transmission link while each of the number of secondary electrical consuming devices are operating.

6. The medical imaging device of claim 1, wherein a main electrical consuming device comprises a radiation source.

7. The medical imaging device of claim 1, wherein a secondary electrical consuming device comprises a radiation detector, or a motor, or a data processing unit.

8. The medical imaging device of claim 1, further comprising:
    at least one of a transformer and a rectifier, wherein the at least one of the transformer and the rectifier is disposed in a switching path between each of the number of main electrical consuming devices and the power transmission link and between each of the number of secondary electrical consuming devices and the power transmission link.

9. The medical imaging device of claim 1, wherein the energy storage device is configured to maintain baseload operation of each of the number of secondary electrical consuming devices at least for a time period in the event of failure of the power source.

10. The medical imaging device of claim 1, wherein the energy storage device comprises at least one of a battery and a capacitor.

11. The medical imaging device of claim 1, wherein the power transmission link comprises at least one of a slip ring contact and a number of transmission coils.

12. The medical imaging device of claim 1, wherein the movable device section is rotatable mounted about an axis.

13. The medical imaging device of claim 1, further comprising:
    a computed tomography scanner, wherein the fixed device section comprises a support frame and the movable device section comprises a rotating ring, wherein each of the number of main electrical consuming devices comprises an X-ray tube, and wherein a secondary electrical consuming device comprises an X-ray detector.

14. The medical imaging device of claim 1, further comprising a control unit, connected to the at least one switching device, configured to at least:
    switchably connect the energy storage device to each of the number of secondary electrical consuming devices;

charge the energy storage device by the power source via the power transmission link;

supply, during baseload operation, each of the number of secondary electrical consuming devices from the power source via the power transmission link; and supply, during main load operation, each of the number of main electrical consuming devices by the power source via the power transmission link while each of the number of secondary electrical consuming devices is supplied by the energy storage device.

15. A method for supplying power to a medical imaging device including:

a fixed device section, a movable device section, movably mounted, a power source to provide power, disposed on the fixed device section, a number of main electrical consuming devices, a number of secondary electrical consuming devices, and an energy storage device, each disposed on the movable device section, at least one switching device, and a power transmission link including an energy supplying component and an energy receiving component, configured to transmit power from the fixed device section to the movable device section, disposed between the fixed device section and the movable device section, the energy supplying component on the fixed device section, being connected to the power source, and the energy receiving component on the movable device section being switchably connected to each of the number of main electrical consuming devices and to each of the number of secondary electrical consuming devices via the at least one switching device and being switchably connected to the energy storage device, the method comprising:

switchably connecting the energy storage device to each of the number of secondary electrical consuming devices;

charging the energy storage device by the power source via the power transmission link;

supplying, during baseload operation, each of the number of secondary electrical consuming devices from the power source via the power transmission link; and supplying, during main load operation, each of the number of main electrical consuming devices by the power source via the power transmission link while each of the number of secondary electrical consuming devices is supplied by the energy storage device.

16. The method of claim 15, wherein the energy storage device is supplied during baseload operation while each of the number of secondary electrical consuming devices is simultaneously supplied at least intermittently.

\* \* \* \* \*